US012662134B2

(12) United States Patent
Hwang

(10) Patent No.: US 12,662,134 B2
(45) Date of Patent: Jun. 23, 2026

(54) DRIVER ASSISTANCE SYSTEM AND METHOD USING ELECTROENCEPHALOGRAM

(71) Applicant: HYUNDAI MOBIS CO., LTD., Seoul (KR)

(72) Inventor: Jong Ho Hwang, Seoul (KR)

(73) Assignee: Hyundai Mobis Co., Ltd., Seoul (KR)

( * ) Notice: Subject to any disclaimer, the term of this patent is extended or adjusted under 35 U.S.C. 154(b) by 173 days.

(21) Appl. No.: 18/339,637

(22) Filed: Jun. 22, 2023

(65) Prior Publication Data

US 2024/0199033 A1     Jun. 20, 2024

(30) Foreign Application Priority Data

Dec. 19, 2022     (KR) ........................ 10-2022-0178141

(51) Int. Cl.
*B60W 40/09*          (2012.01)
*A61B 5/291*          (2021.01)
(Continued)

(52) U.S. Cl.
CPC ............. *B60W 40/09* (2013.01); *A61B 5/291* (2021.01); *A61B 5/369* (2021.01); *B60W 40/08* (2013.01); *B60W 50/0098* (2013.01); *B60W 50/045* (2013.01); *B60W 50/14* (2013.01); *G06F 3/015* (2013.01); *B60W 2040/0872* (2013.01); *B60W 2050/143* (2013.01); *B60W 2050/146* (2013.01); *B60W 2540/221* (2020.02); *B60W 2540/229* (2020.02)

(58) Field of Classification Search
CPC ... G06F 3/015; A61B 5/18; A61B 5/291–293; A61B 5/31; A61B 5/369–385; B60W 40/08; B60W 40/09; B60W 2040/0818–089; B60W 50/0098; B60W 50/045; B60W 50/14; B60W 2050/0052; B60W 2050/143; B60W 2050/146; B60W 2540/221; B60W 2540/229
See application file for complete search history.

(56) References Cited

U.S. PATENT DOCUMENTS

| | | | | |
|---|---|---|---|---|
| 5,813,993 | A * | 9/1998 | Kaplan | ................ A61B 5/7203 |
| | | | | 600/26 |
| 11,433,916 | B1 * | 9/2022 | Faizan | ................ A61B 5/0077 |

(Continued)

FOREIGN PATENT DOCUMENTS

| | | | | |
|---|---|---|---|---|
| CN | 114228724 A | * | 3/2022 | ............. A61B 5/369 |
| DE | 102010007241 A1 | * | 9/2010 | ............. A61B 5/048 |

(Continued)

*Primary Examiner* — John M Zaleskas
(74) *Attorney, Agent, or Firm* — NSIP Law

(57) ABSTRACT

A driver assistance system and method using an electroencephalogram (EEG) is provided where driver assistance system using an electroencephalogram (EEG) includes an EEG measurer configured to measure an EEG signal of a driver of a vehicle, a processor configured to receive a behavior signal of the vehicle indicating a behavior of the vehicle, determine whether the EEG signal is a normal signal, and provide a notification based on determining that the EEG signal is not a normal signal and based on the behavior signal of the vehicle.

11 Claims, 9 Drawing Sheets

(51) Int. Cl.

| | |
|---|---|
| *A61B 5/369* | (2021.01) |
| *B60W 40/08* | (2012.01) |
| *B60W 50/00* | (2006.01) |
| *B60W 50/04* | (2006.01) |
| *B60W 50/14* | (2020.01) |
| *G06F 3/01* | (2006.01) |

(56) References Cited

U.S. PATENT DOCUMENTS

| | | | | |
|---|---|---|---|---|
| 2012/0212353 | A1* | 8/2012 | Fung | G08G 1/167 |
| | | | | 701/1 |
| 2013/0226408 | A1* | 8/2013 | Fung | G08G 1/166 |
| | | | | 701/1 |
| 2013/0245886 | A1* | 9/2013 | Fung | B60W 50/14 |
| | | | | 701/1 |
| 2014/0309881 | A1* | 10/2014 | Fung | B60K 28/06 |
| | | | | 701/36 |
| 2014/0371984 | A1* | 12/2014 | Fung | G08G 1/166 |
| | | | | 701/1 |
| 2016/0023666 | A1* | 1/2016 | Lee | A61B 5/18 |
| | | | | 701/33.4 |
| 2016/0152233 | A1* | 6/2016 | Fung | B60K 28/06 |
| | | | | 701/41 |
| 2017/0090475 | A1* | 3/2017 | Choi | A61B 5/318 |
| 2017/0143270 | A1* | 5/2017 | Song | B60N 2/0023 |
| 2017/0303842 | A1* | 10/2017 | Yoshida | B60W 50/14 |
| 2017/0311831 | A1* | 11/2017 | Freer | A61B 5/16 |
| 2017/0325732 | A1* | 11/2017 | Kodama | A61B 5/18 |
| 2018/0072310 | A1* | 3/2018 | Fung | B60W 50/14 |
| 2018/0186234 | A1* | 7/2018 | Mestha | A61B 5/18 |
| 2018/0297603 | A1* | 10/2018 | Jun | G08G 1/167 |
| 2019/0038166 | A1* | 2/2019 | Tavabi | G06F 3/015 |
| 2019/0046100 | A1* | 2/2019 | Li | B60W 40/08 |
| 2019/0061525 | A1* | 2/2019 | Ji | A61B 5/163 |
| 2019/0121356 | A1* | 4/2019 | Migneco | A61B 5/0205 |
| 2019/0161091 | A1* | 5/2019 | An | G05D 1/0061 |
| 2019/0267847 | A1* | 8/2019 | Yoshida | G08G 1/16 |
| 2020/0122746 | A1* | 4/2020 | Sugiura | B60W 60/0053 |
| 2020/0172091 | A1* | 6/2020 | Takasaki | G08G 1/0145 |
| 2020/0346665 | A1* | 11/2020 | Araújo | A61B 5/163 |
| 2021/0077005 | A1* | 3/2021 | Ambeck-Madsen | A61B 5/18 |
| 2021/0093241 | A1* | 4/2021 | Ambeck-Madsen | A61B 5/7267 |
| 2021/0195981 | A1* | 7/2021 | Ghaffarzadegan | B60W 50/0098 |
| 2021/0213958 | A1* | 7/2021 | Hassani | G06N 3/044 |
| 2021/0269043 | A1* | 9/2021 | Takahashi | A61B 5/18 |
| 2021/0407295 | A1* | 12/2021 | Chang | B60W 40/08 |
| 2022/0063631 | A1* | 3/2022 | Hassani | B60W 40/08 |
| 2022/0369978 | A1* | 11/2022 | Lim | B60K 35/26 |
| 2024/0199085 | A1* | 6/2024 | Kim | A61B 5/0205 |
| 2024/0217533 | A1* | 7/2024 | Lim | A61B 5/165 |

FOREIGN PATENT DOCUMENTS

| | | | | | |
|---|---|---|---|---|---|
| DE | 102018221271 | A1 | * | 6/2020 | |
| GB | 2465439 | A | * | 5/2010 | A61B 5/0476 |
| JP | 2014089557 | A | * | 5/2014 | |
| KR | 970065230 | A | * | 10/1997 | |
| KR | 101447060 | B1 | * | 10/2014 | |
| KR | 101632830 | B1 | * | 6/2016 | |
| KR | 20180042742 | A | * | 4/2018 | |
| KR | 20200046612 | A | * | 5/2020 | |
| KR | 20200088921 | A | * | 7/2020 | |
| KR | 20210103035 | A | * | 8/2021 | B60H 1/00814 |
| WO | WO-2014092494 | A1 | * | 6/2014 | A61B 5/04845 |
| WO | WO-2016035268 | A1 | * | 3/2016 | A61B 5/0476 |

* cited by examiner

| Item | Notification OFF | Notification ON | Sum |
|---|---|---|---|
| Driving time (sec) | 1891569 | 1719330 | 3610899 |
| Number of notifications according to related art | 14734 | 9608 | 24342 |
| Number of notifications according to new criterion | 690 (Decrease of 95.32%) | 596 (Decrease of 93.80%) | 1286 (Decrease of 94.72%) |

FIG. 9

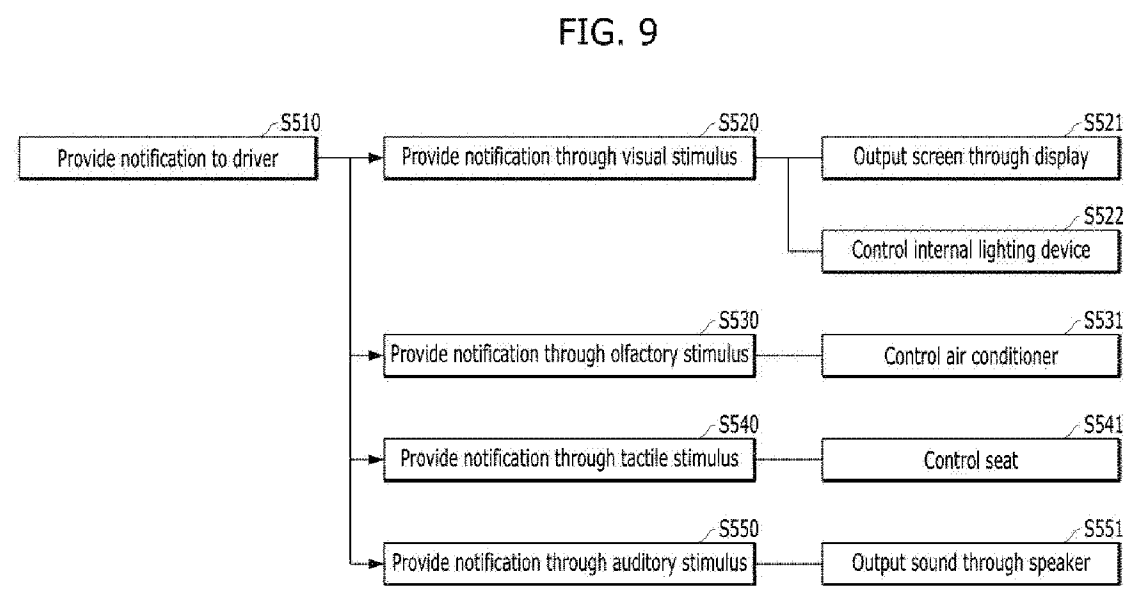

S510 — Provide notification to driver

S520 — Provide notification through visual stimulus
- S521 — Output screen through display
- S522 — Control internal lighting device S530 — Provide notification through olfactory stimulus
- S531 — Control air conditioner S540 — Provide notification through tactile stimulus
- S541 — Control seat S550 — Provide notification through auditory stimulus
- S551 — Output sound through speaker

DRIVER ASSISTANCE SYSTEM AND METHOD USING ELECTROENCEPHALOGRAM

CROSS-REFERENCE TO RELATED APPLICATIONS

This application claims the benefit under 35 U.S.C. § 119(a) to Korean Application No. 10-2022-0178141, filed on Dec. 19, 2022, in the Korean Intellectual Property Office, the entire disclosure of which is incorporated herein by reference for all purposes.

BACKGROUND

1. Field

The present disclosure relates to a driver assistance system and method using an electroencephalogram (EEG), which enhance reliability in determining negligence of a driver through an EEG signal of the driver and prevent an unnecessary notification from being provided by considering a behavior signal of a vehicle together with the EEG signal.

2. Description of Related Art

In modern society, vehicles are explosively increasing as incomes rise and consumers seek convenience. In addition, the increase in vehicles has caused various traffic accidents, resulting in an increase in casualties. In order to minimize casualties in these traffic accidents, countries around the world are making great efforts to develop safe vehicles.

Safe vehicles are vehicles that reduce fatalities in the event of traffic accidents, reduce driver fatigue, and are convenient to drive. The basic concept of safe vehicles is to improve vehicle safety and prevent accidents to protect pedestrians.

Despite various safe devices installed in a vehicle, negligence of a driver is directly related to fatal accidents. In particular, when a driver drives while tired, there is the case in which he or she becomes drowsy during driving without even realizing it. Studies have shown that drowsy driving increases the risk of traffic accidents by more than 8 times than usual.

If the driver of a vehicle traveling at 90 km/h dozes off for 4 or 5 seconds, it is like traveling 100 to 125 m without a driver. In particular, in the case of highways, since most vehicles travel at a speed of 100 km per hour or more, drowsy driving inevitably leads to very dangerous results.

Recently, in order to provide a more convenient interface to users, attempts have been made to develop a human-friendly interface using biosignals such as voice, facial expressions, gestures, an EEG, an electrooculogram, and an electromyogram.

An EEG is a representative biosignal that directly or indirectly reflects a human's conscious or unconscious state. The EEG is measured in all regions of the human scalp and has a wavelength with a frequency of 50 Hz or less with a potential difference of several tens of microvolts.

The EEG may be classified into delta waves, theta waves, alpha waves, beta waves, gamma waves, and the like according to the wavelength of a frequency.

The delta waves are an EEG with a frequency of less than 4 Hz and are typically found when a person is normally asleep. The theta waves are an EEG with a frequency of about 4 to 8 Hz. Theta waves are mainly found when a person is mentally unstable or distracted and occur when a person is drowsy or falls asleep. The alpha waves are an EEG with a frequency of about 8 to 12 Hz and are clearly found when a person is in a stable mental state and is in a comfortable psychological state with eyes closed. The beta waves refer to an EEG with a frequency of about 12 to 30 Hz. The beta waves are more strongly found when a person is under stress, such as a little anxiety or tension, and are mainly observed when a person is paying more than a certain amount of attention. The gamma waves are an EEG with a frequency of 30 to 50 Hz and are found in a state of extreme arousal and excitement.

As described above, a driver requires considerable concentration while driving a vehicle. If a driver is negligent for a moment while driving, an accident resulting in damage to the vehicle and human life may occur. This negligence of the driver causes a large-scale accident that not only injures the driver but also injures others.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a driver assistance system using an electroencephalogram (EEG) including an EEG measurer configured to measure an EEG signal of a driver of a vehicle, a processor configured to receive a behavior signal of the vehicle indicating a behavior of the vehicle, determine whether the EEG signal is a normal signal, and provide a notification based on determining that the EEG signal is not a normal signal and based on the behavior signal of the vehicle.

The driver assistance system may include a storage configured to store the EEG signal determined to be the normal signal, wherein the processor may be configured to determine whether the EEG signal is the normal signal by comparing EEG signals stored in the storage with the EEG signal.

The processor may be configured to determine whether the EEG signal is the normal signal based on a window size of a preset unit time.

The processor may be configured to control the EEG measurer based on the window size, in response to determining that the EEG signal is an abnormal signal.

The processor may be configured to determine whether the EEG measurer is normally worn based on the EEG signal and to provide another notification to the driver upon determining that the EEG measurer is abnormally worn.

The processor may be configured to remove noise included in the EEG signal determined to be the normal signal and to extract a feature point by analyzing a frequency component of the EEG signal from which the noise has been removed.

The processor may be configured to remove the noise through a direct current (DC) offset of an amplitude of the EEG signal determined to be the normal signal or to remove the noise through any one of a noise filter, a high-pass filter, a low-pass filter, a band-pass filter, a notch filter, or an active filter.

The behavior signal of the vehicle may include a driving mode signal, and the driving mode signal may include a stop mode signal, a low-speed driving mode signal, and a high-speed driving mode signal.

The processor may be configured to determine whether to provide the notification based on a number of times the driver is negligent per unit time according to the driving mode signal.

The processor may be configured to determine whether to provide the notification based on whether the driving mode signal is changed.

The processor may be configured to provide the notification to the driver by controlling a vehicle including at least one of a display, an internal lighting device, an air conditioner, a seat, or a speaker of the vehicle.

In another general aspect, there is provided a processor-implemented driver assistance method using an electroencephalogram (EEG), the method including measuring an EEG signal of a driver of a vehicle through an EEG measurer, receiving a behavior signal of the vehicle, determining whether the EEG signal is a normal signal, and providing a notification in response to determining that the EEG signal is not a normal signal and based on the behavior signal.

The driver assistance method may include storing the EEG signal determined to be the normal signal, and the determining of whether the EEG signal is the normal signal comprises comparing the stored EEG signals with the EEG signal.

The determining of whether the EEG signal is the normal signal may be based on a window size of a preset unit time.

The driver assistance method may include controlling the EEG measurer based on the window size, in response to determining that the EEG signal is an abnormal signal.

The driver assistance method may include determining whether the EEG measurer is normally worn based on the EEG signal, and providing another notification to the driver upon determining that the EEG measurer is abnormally worn.

The determining of whether the driver is negligent may include removing noise included in the EEG signal determined to be the normal signal and extracting a feature point by analyzing a frequency component of the EEG signal from which the noise has been removed.

The removing the noise may include removing the noise through a direct current (DC) offset of an amplitude of the EEG signal determined to be the normal signal or removing the noise through any one of a noise filter, a high-pass filter, a low-pass filter, a band-pass filter, a notch filter, or an active filter.

The behavior signal of the vehicle may include a driving mode signal, and the driving mode signal may include a stop mode signal, a low-speed driving mode signal, and a high-speed driving mode signal, and wherein the providing of the notification may include providing the notification, in response to a number of times the driver is negligent per unit time according to the driving mode signal.

The determining of whether to provide the notification may include determining to provide the notification in response to the driving mode signal being changed.

In another general aspect, there is provided a method of controlling rendering, within a compartment of a vehicle, of a notification, the method including monitoring an EEG signal of a driver of the vehicle and determining when the driver is in a first state and when the driver is in a second state, receiving indications of a driving mode of the vehicle, wherein the driving mode changes between a first mode and a second mode, based on the driver being determined to be in the first state and based on the driving mode being in the first mode, performing a first rendering, within a compartment of the vehicle, of a notification comprising one or more of an audio notification, a haptic notification, or a visual notification, and based on the driver being determined to be in the second state and based on the driving mode being in the second mode, performing a second rendering, within the compartment of the vehicle, of a notification comprising one or more of an audio notification, a haptic notification, or a visual notification.

Other features and aspects will be apparent from the following detailed description, the drawings, and the claims.

BRIEF DESCRIPTION OF DRAWINGS

FIG. 2 is a diagram illustrating a method in which the driver assistance system according to an embodiment of the present disclosure determines whether an electroencephalogram (EEG) measurer is normally worn.

FIG. 5 is a table illustrating an effect of preventing a notification from being incorrectly provided through the driver assistance system according to an embodiment of the present disclosure.

FIG. 9 is a diagram illustrating various embodiments of providing a notification to a driver in a driver assistance method of the present disclosure.

Figure 1:
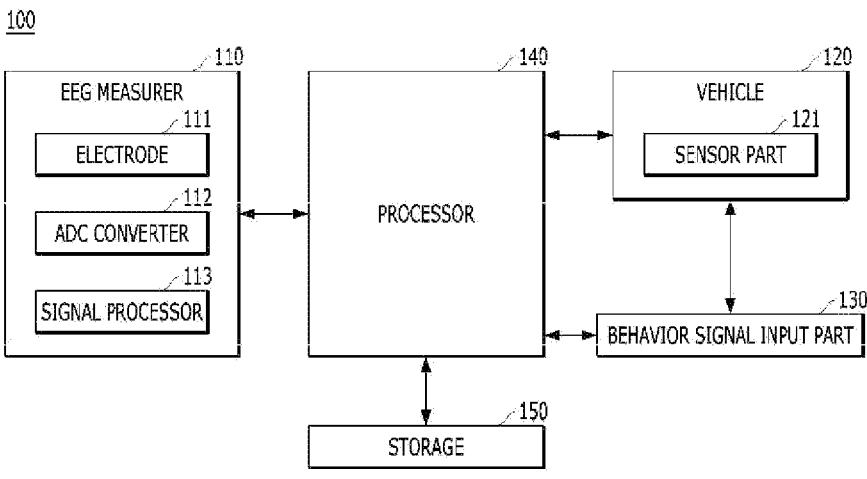
FIG. 1 is a block diagram of a driver assistance system according to an embodiment of the present disclosure.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known after an understanding of the disclosure of this application may be omitted for increased clarity and conciseness.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Although the terms first, second, etc. may be used herein to describe various elements, these elements should not be limited by these terms. These terms are generally only used to distinguish one element from another.

It will be understood that when an element is referred to as being "connected with" another element, the element can be directly connected with the other element or intervening elements may also be present. In contrast, it will be understood that when an element is referred to as being "directly connected with" another element, there are no intervening elements present.

A singular representation may include a plural representation unless it represents a definitely different meaning from the context.

The terms such as "include" or "have" used herein are intended to indicate that features, numbers, steps, operations, elements, components, or combinations thereof used in the following description exist and it should be thus understood that the possibility of existence or addition of one or more different features, numbers, steps, operations, elements, components, or combinations thereof is not excluded.

Figure 2:
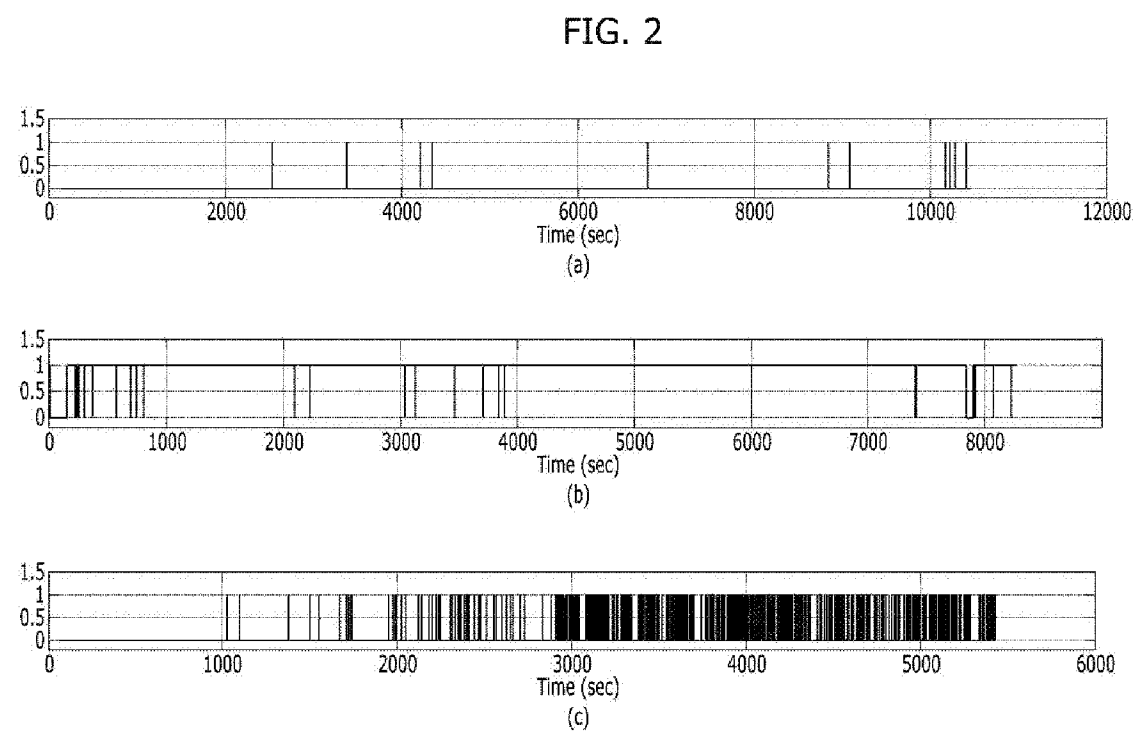
Figure 3:
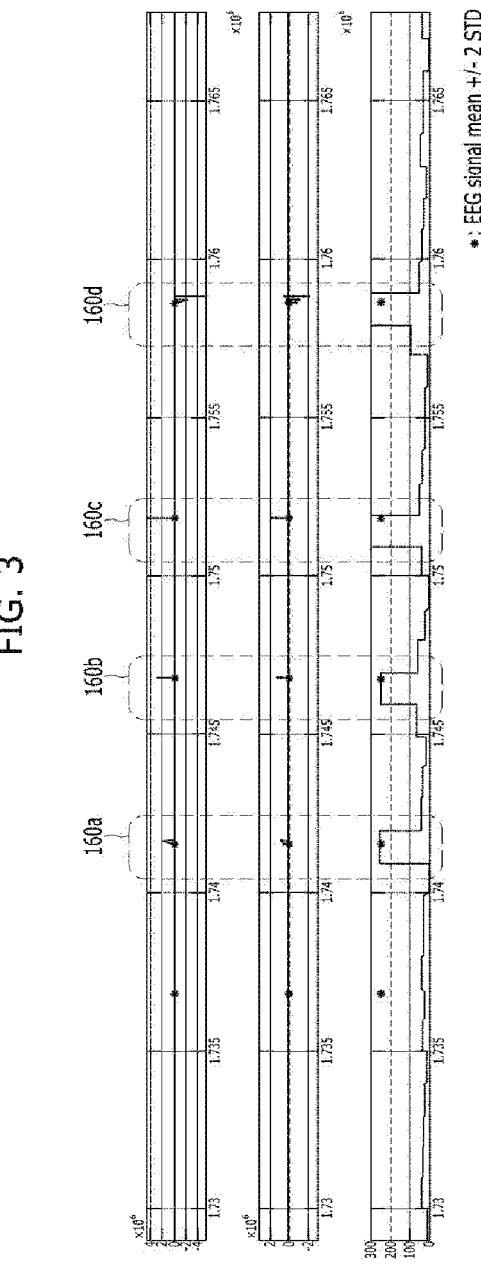
FIGS. 3 and 4 are diagrams illustrating a method in which the driver assistance system according to an embodiment of the present disclosure determines that a measured EEG signal is an abnormal signal.
Figure 4:
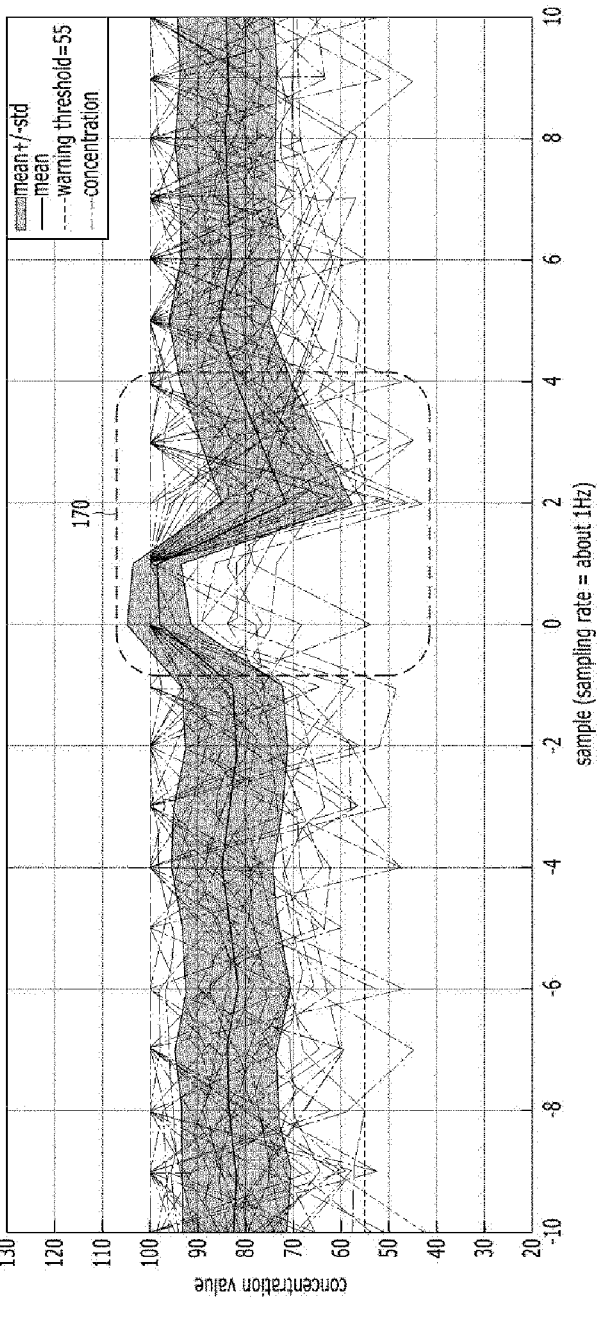

FIG. 1 is a block diagram of a driver assistance system 100 according to an embodiment of the present disclosure. FIG. 2 is a diagram illustrating a method in which the driver assistance system 100 according to an embodiment of the present disclosure determines whether an electroencephalogram (EEG) measurer 110 is normally worn. FIGS. 3 and 4 are diagrams illustrating a method in which the driver assistance system 100 according to an embodiment of the present disclosure determines that a measured EEG signal is an abnormal signal.

Referring first to FIG. 1, the driver assistance system 100 according to an embodiment of the present disclosure may include the EEG measurer 110, a behavior signal input part 130, a processor 140, and a storage 150.

An EEG is generated by communication of thought, emotion, and behaviors of an object between neurons in the brain and is a synchronized electrical wave generated while neurons in the cerebral cortex transmit signals to each other.

The EEG may be measured through an electroencephalography test that measures a potential difference between surface electrodes placed in a specific area of the scalp. The EEG produced by electroencephalography is the sum of electrical activities of countless cerebral cortex neurons beneath the surface electrodes.

As described above, the EEG appears as various frequency bands. More specifically, the EEG may be classified into delta waves, theta waves, alpha waves, beta waves, and gamma waves, etc. according to the frequency bands.

In the driver assistance system 100 according to an embodiment of the present disclosure, the EEG measurer 110 may measure an EEG signal of a driver. The EEG measurer 110 may be connected to devices that measure the EEG signal of the driver. In one embodiment, the EEG measurer 110 may be in contact with the scalp through an electrode 111 to directly measure the EEG signal of the driver. The EEG measurer 110 may include an earset including the electrode 111, that contacts the driver and receives the EEG signal. The earset may include the electrode 111 of a single channel and the electrode 111 may have conductivity. Accordingly, the EEG measurer 110 may easily measure the EEG signal of the driver using the earset that the driver may easily wear.

As another embodiment, the EEG measurer 110 may include a headset using the electrode 111 of multiple channels. The EEG measurer 110 may further include the EEG electrode 111 in contact with the driver, the reference electrode 111, and the ground electrode 111.

Furthermore, in the driver assistance system 100 according to an embodiment of the present disclosure, the EEG measurer 110 may include various sensors or devices for measuring the EEG signal of the driver in real time, including the above-described earset and headset.

Additionally, the EEG measurer 110 may further include an analog-to-digital (ADC) converter 112 that converts an EEG signal (analog signal) into a digital signal. According to an embodiment of the present disclosure, the EEG measurer 110 may further include a signal processor 113 that wirelessly transmits the EEG signal to the processor 140 using communication such as Bluetooth, infrared communication, radio frequency identification (RFID), ultra-wideband (UWB), or the like or transmits the EEG signal to the processor 140 by wire.

In the driver assistance system 100 according to an embodiment of the present disclosure, the behavior signal input part 130 may receive a behavior signal of a vehicle 120. The behavior signal input part 130 may receive the behavior signal of the vehicle 120 through a sensor part 121 located in the vehicle 120. As an example, the sensor unit 121 may include all sensors located in the vehicle 120, including a brake sensor, a tilt sensor, a lidar sensor, a global positioning system (GPS) sensor, and the like.

The driver assistance system 100 receives the behavior signal of the vehicle 120 through the behavior signal input part 130 and provides a notification to a driver according to negligence of the driver together with the EEG signal. In addition, the driver assistance system 100 considers the behavior signal of the vehicle 120 together with the EEG signal and thus an unnecessary notification is prevented from being provided. Details on this will be described later.

In the driver assistance system 100 according to an embodiment of the present disclosure, the processor 140 may determine whether the EEG signal measured by the EEG measurer 110 is a normal signal and determine whether the driver is negligently driving based on the EEG signal determined to be the normal signal and the behavior signal received through the behavior signal input part 130, thereby providing a notification.

In general, whether the driver is negligently driving may be determined through the EEG signal of the driver. In this case, however, the EEG signal may not be a normal signal depending on the state of the driver, such as the movement of the driver. When negligence of the driver is determined based on an abnormal EEG signal, reliability in determining negligence of the driver naturally decreases.

According to the present disclosure, the processor 140 may determine whether the EEG signal measured by the EEG measurer 110 is a normal signal in order to solve the above issue. To this end, the driver assistance system 100 may include the storage 150 that stores the EEG signal determined to be a normal signal.

According to an embodiment, the processor 140 may determine whether the measured EEG signal is a normal signal by comparing the EEG signal stored in the storage 150 with the EEG signal measured by the behavior signal input part 130. Further, the processor 140 may determine whether the driver is normally wearing the EEG measurer 110 through the EEG signal measured by the EEG measurer 110.

That is, the processor 140 of the present disclosure may determine whether the driver is normally wearing the EEG measurer 110 and determines whether the EEG signal measured while the driver is wearing the EEG measurer 110 is a normal signal. Therefore, determination as to whether the driver is negligently driving based on an abnormal EEG signal according to a state such as movement of the driver may be prevented. Therethrough, reliability in determining negligence of the driver may be increased.

In connection with reliability in determining negligence of the driver, the driver assistance system 100 according to an embodiment of the present disclosure may provide a notification instructing the driver to normally wear the EEG measurer 110 again when the driver is abnormally wearing the EEG measurer 110.

FIG. 2 is a diagram illustrating a method in which the driver assistance system 100 according to an embodiment of the present disclosure determines whether the EEG measurer 110 is normally worn. FIG. 2 is a graph over time, expressing the case in which the EEG measurer 110 is worn as 1 and the case in which the EEG measurer 110 is not worn as 0. FIG. 2A is a graph when the EEG measurer 110 is not worn and FIG. 2B is a graph when the EEG measurer 110 is worn. In FIGS. 20, 0 and 1 are continuously repeated irregularly at short time intervals. Therethrough, it may be seen that FIG. 2C is a graph when the EEG measurer 110 is abnormally worn.

FIGS. 3 and 4 are diagrams illustrating a method in which the driver assistance system 100 according to an embodiment of the present disclosure determines that a measured EEG signal is an abnormal signal.

As described above with reference to FIG. 1, the processor 140 in the driver assistance system 100 according to an embodiment of the present disclosure determines whether the EEG signal measured by the EEG measurer 110 is a normal signal in order to increase reliability in determining negligence of a driver. In this case, the processor 140 may determine whether the measured EEG signal is a normal signal by comparing the EEG signal stored in the storage 150 with the measured EEG signal.

The processor 140 may determine whether the measured EEG signal is a normal signal through a window size 170 of a preset unit time. The processor 140 may control the EEG measurer 110 based on the window size 170 when the measured EEG signal is determined to be an abnormal signal. That is, the processor 140 may control the EEG measurer 110 to start measurement of the EEG signal after a time equal to the window size 170 of the preset unit time has elapsed.

When the measured EEG signal is determined to be an abnormal signal through the window size 170, the processor 140 may not utilize the EEG signal corresponding to the window size 170 in order to increase reliability in determining negligence of the driver.

FIG. 3 is a diagram illustrating abnormal signal regions 160a, 160b, 160c, and 160d in which the EEG signal measured by the EEG measurer 110 is determined to be an abnormal signal. According to an embodiment, the processor 140 may determine whether the measured EEG signal is an abnormal signal through a standard deviation (STD) value of the EEG signal.

FIG. 4 is a diagram illustrating an example of extracting an abnormal signal from a measured EEG signal through the window size 170. As described above, the driver assistance system 100 according to an embodiment of the present disclosure may not use an abnormal signal corresponding to the window size 170 and the processor 140 may control the EEG measurer 110 such that the EEG signal is measured again after a time equal to the window size 170 has elapsed.

After determining whether the EEG measurer 110 is normally worn and determining whether the EEG signal measured by the EEG measurer 110 is a normal signal, the processor 140 may remove noise included in the EEG signal determined to be the normal signal. The processor 140 may then extract a feature point by analyzing a frequency component of the EEG signal from which noise has been removed.

Here, noise may include not only noise generated by eye-blink of the driver, AC power noise, and DC drift components, but also all factors interfering with extraction of the feature point.

The processor 140 may remove noise through a DC offset of the amplitude of the EEG signal determined to be the normal signal. The processor 140 may remove noise included in the EEG signal using various filters. In one embodiment, the processor 140 may remove noise using any one of a noise filter, a high-pass filter, a low-pass filter, a band-pass filter, a notch filter, and an active filter.

The processor 140 may extract a feature point by analyzing a frequency component including at least one of the gamma, beta, alpha, theta, delta, or SMR (Sensory Motor Rhythm) frequency band in the EEG signal. More specifically, the processor 140 may analyze the frequency component by performing Fourier transform on the EEG signal measured by the EEG measurer 110.

Here, the Fourier transform is a concept including both fast Fourier transform (FFT) and short-time Fourier transform (STFT).

The processor 140 may classify the EEG signal into a plurality of bands according to the frequency component, calculate power spectral density for each band, and extract a feature point according to the magnitude of the calculated spectral density. The processor 140 may also extract a feature point related to the size of power spectral density for each band.

FIG. 5 is a table illustrating an effect of preventing a notification from being incorrectly provided through the driver assistance system 1000 according to an embodiment of the present disclosure.

The driver assistance system 100 according to an embodiment of the present disclosure not only improves reliability in determining negligence of a driver, but also prevents an unnecessary notification from being provided by considering a behavior signal of the vehicle 120 together with the EEG signal.

As described above with reference to FIG. 1, the driver assistance system 100 of the present disclosure includes the behavior signal input part 130 that receives the behavior signal of the vehicle 120. The behavior signal may include a driving mode signal of the vehicle 120. Here, the driving mode signal may include a stop mode signal, a low-speed driving mode signal, and a high-speed driving mode signal. Such a driving mode signal may be determined through information obtained through the sensor part 121 of the vehicle 120 described above. For example, the driving mode signal of the vehicle 120 may be determined to be the stop mode signal when a gear rod of the vehicle 120 is placed at a P or N position or when the driver is depressing a brake for a predetermined time or more. When the behavior signal of the vehicle 120 is the stop mode signal, the processor 140 may control the behavior signal input part 130 to continuously receive a signal.

The processor 140 may consider the number of times determined to be negligent of the driver per preset unit time according to the driving mode signal. Therethrough, it may be determined whether to provide a notification to the driver. Here, the processor 140 may determine whether to provide the notification to the driver by considering whether the driving mode signal is changed.

In more detail, when the vehicle 120 is not stationary but is driving, it is necessary to consider the behavior signal of the vehicle 120. In particular, a traveling speed and a maintenance time of the speed need to be considered. This is because providing the notification to the driver may be more important since the risk of an accident caused by negligence of the driver is greater in high-speed driving than in low-speed driving. In addition, the risk of an accident due to carelessness of the driver is greater when the vehicle 120 changes from low-speed driving to high-speed driving than when the vehicle 120 changes from high-speed driving to low-speed driving.

Reflecting this point, in the driver assistance system 100 according to an embodiment of the present disclosure, the processor 140 may control provision of the notification to the driver by determining whether to provide the notification according to the number of times determined to be negligence of the driver per preset unit time, that is, by determining sensitivity of a decision logic for providing the notification.

Therefore, in the case of low-speed driving, changing from high-speed driving to low-speed driving, or driving of the vehicle 120 at the same speed, sensitivity of the above-described decision logic may be somewhat lowered. For example, when three times or more are determined to be negligence of the driver within 5 seconds, the notification may be provided to the driver through the processor 140.

On the contrary, that is, in the case of high-speed driving or changing from low-speed driving to high-speed driving, the above-described decision logic needs to be changed to be somewhat sensitive. For example, when twice or even once within 5 seconds is determined to be negligence of the driver, the notification may be immediately provided to the driver.

As shown in FIG. 5, in the case of an embodiment using a new criterion through a change in sensitivity of the above-described decision logic, the probability of incorrectly providing a notification may be reduced and an unnecessary notification may be prevented from being provided to the driver.

Figure 6:
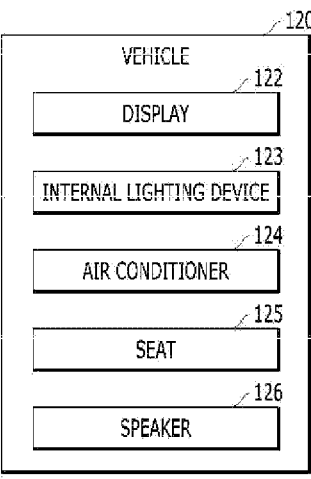
FIG. 6 is a diagram illustrating a configuration of a vehicle that provides a notification to a driver in the driver assistance system according to an embodiment of the present disclosure.

FIG. 6 is a diagram illustrating a configuration of the vehicle 120 that provides a notification to a driver in the driver assistance system 100 according to an embodiment of the present disclosure.

In the present disclosure, the processor 140 may provide a driver with a notification through a stimulus in various ways. The processor 140 may provide the notification through a display 122, an internal lighting device 123, an air conditioner 124, a seat 125, and/or a speaker 126 located in the vehicle 120.

The processor 140 may provide the notification to the driver through a visual stimulus including output of a screen through the display 122 of the vehicle 120 or including control of the internal lighting device 123 of the vehicle 120. The display 122 may include both a center information display (CID) and a head-up display (HUD). In one embodiment, the processor 140 may control the intensity of the lighting device or the wavelength (color of light) of the lighting device. In particular, the lighting device 123 may be a mood lighting device in the vehicle 120 or an ambient lighting device.

In addition, the processor 140 may provide the notification to the driver through an olfactory stimulus including control of an indoor temperature through the air conditioner 124 of the vehicle 120 or introduction of outside air. For example, the processor 140 may control the indoor temperature by operating the air conditioner such that the indoor temperature is lowered when concentration of the driver decreases. In order to lower carbon dioxide concentration, the processor 140 may control a mode to be to an exterior circulation mode such that outside air is introduced into the vehicle 120 and control the air conditioner 124 to generate an olfactory stimulus to the driver using an air freshener or the like.

The processor 140 may provide the notification to the driver through a tactile stimulus including control of at least one of a massage device, a ventilation device, or a variable device installed on the seat 125 of the vehicle 120. In addition, the processor 140 may provide the notification to the driver through an auditory stimulus including output of sound through the speaker 126 of the vehicle 120.

Figure 7:
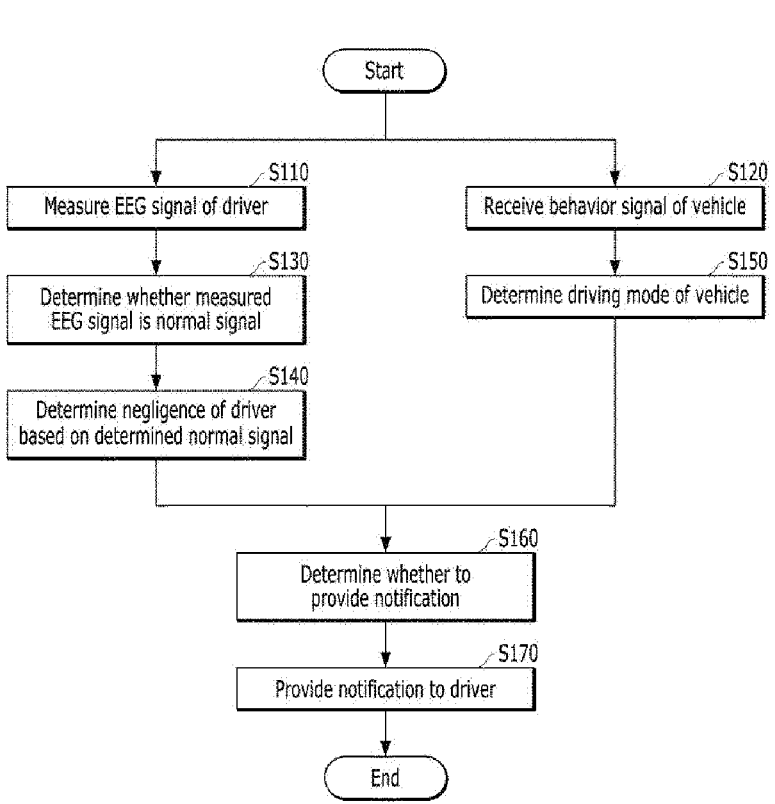
FIG. 7 is a diagram illustrating a driver assistance method according to an embodiment of the present disclosure.
Figure 8:
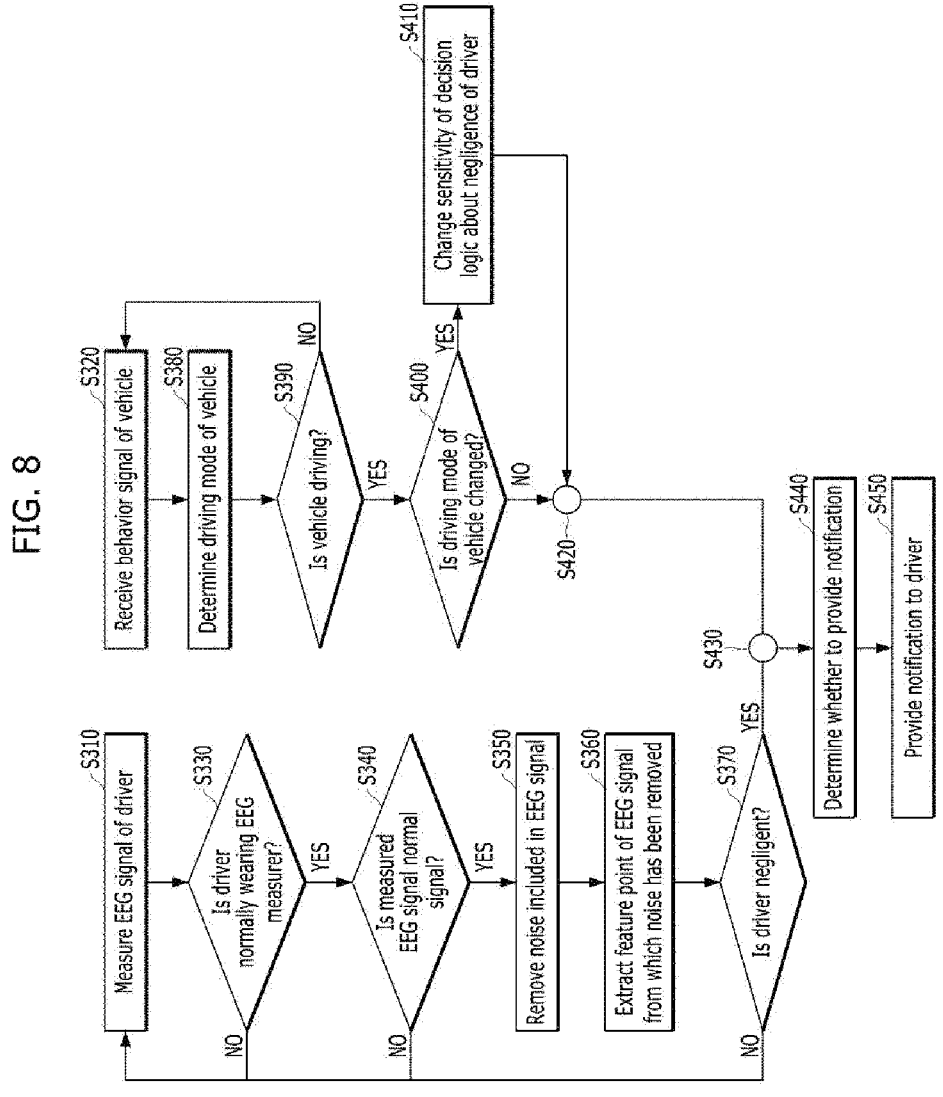
FIG. 8 is a diagram illustrating the driver assistance method of FIG. 7 in more detail.

FIG. 7 is a diagram illustrating a driver assistance method according to an embodiment of the present disclosure. FIG. 8 is a diagram illustrating the driver assistance method of FIG. 7 in more detail.

First, an EEG signal of a driver may be measured (S110), and simultaneously a behavior signal of a vehicle may be received (S120). Here, the EEG signal of the driver may be measured through the EGG measurer. Thereafter, whether the measured EEG signal is a normal signal is determined (S130), and negligence of the driver may be determined based on the determined normal signal (S140). The behavior signal of the vehicle may include a driving mode signal of the vehicle, and a driving mode of the vehicle may be determined (S150). Here, the driving mode of the vehicle may include a stop mode, a low-speed driving mode, and a high-speed driving mode.

It may be determined whether to provide a notification to the driver (S160) and the notification may be provided to the driver (S170).

FIG. 8 is a diagram illustrating the driver assistance method of FIG. 7 in more detail.

An EEG signal of a driver may be measured through the EEG measurer (S310). At the same time, a behavior signal of a vehicle may be received (S320). For convenience of description, a process of determining whether the driver is negligent will be described first.

When measuring the EEG signal, it may be determined whether the driver is normally wearing the EEG measurer (S330). Here, when it is determined that the driver is abnormally wearing the EEG measurer, the procedure returns to measuring the EEG signal of the driver (S310). In this case, a notification instructing the driver to normally wear the EEG measurer may be provided.

When the driver is normally wearing the EEG measurer, it may be determined whether the EEG signal measured by the EEG measurer is a normal signal (S340). This is because the measured EEG signal may not be a normal signal depending on the state of the driver, such as the movement of the driver. That is, if negligence of the driver is determined through an abnormal EEG signal, reliability in determining negligence of the driver may be reduced.

Here, the driver assistance system according to an embodiment of the present disclosure may determine whether the measured EEG signal is a normal signal through a window size of a preset unit time. In addition, when the measured EEG signal is determined to be an abnormal signal, the EEG measurer may be controlled based on the window size. That is, the EEG measurer may be controlled to start measuring the EEG signal after a time equal to the window size of the preset unit time has elapsed.

When the measured EEG signal is determined to be an abnormal signal through the window size, the EEG signal corresponding to the window size may not be used in order to increase reliability in determining negligence of the driver.

When the measured EEG signal is determined to be a normal signal, noise included in the EEG signal may be removed (S350). In addition, a feature point may be extracted by analyzing a frequency component of the EEG signal from which noise has been removed (S360).

Noise may be removed through a DC offset of the amplitude of the EEG signal determined to be a normal signal. In addition, noise included in the EEG signal may be removed using various filters. In one embodiment, noise may be removed through any one of a noise filter, a high-pass filter, a low-pass filter, a band-pass filter, a notch filter, and an active filter.

In addition, the feature point may be extracted by analyzing a frequency component including at least one of a gamma, beta, alpha, theta, delta, or SMR frequency band in the EEG signal. More specifically, the frequency component may be analyzed by performing Fourier transform on the EEG signal measured by the EEG measurer. Here, the Fourier transform is a concept including both FFT and STFT.

In addition, the EEG signal may be categorized into a plurality of bands according to the frequency component and power spectral density for each band may be calculated. The feature point may be extracted according to the size of the calculated spectral density. In addition, a feature point related to the size of power spectral density for each band may be extracted.

Through the above operations, whether the driver is negligent may be determined (S370). When negligence of the driver does not occur, the EEG signal of the driver may be measured again, and therethrough, the EEG signal of the driver may be continuously measured in real time.

After receiving the behavior signal of the vehicle (S320), the driving mode of the vehicle may be determined (S380).

The driver assistance method according to an embodiment of the present disclosure is not only to improve reliability in determining negligence of the driver but also to prevent an unnecessary notification from being provided by considering the behavior signal of the vehicle together with the EEG signal of the driver.

The behavior signal may include a driving mode signal of the vehicle. Here, the driving mode signal may include a stop mode signal, a low-speed driving mode signal, and a high-speed driving mode signal.

It may be determined whether the vehicle is driving (S390). That is, when the vehicle is in a stop mode, the procedure may return to receiving the behavior signal of the vehicle (S320). When the vehicle is driving, that is, when the vehicle is in a low-speed driving mode or a high-speed driving mode, it may be determined whether the driving mode of the vehicle is changed (S400).

This is because it is necessary to consider the behavior signal of the vehicle when the vehicle is driving instead of stationary. In particular, it is necessary to consider a driving speed and the maintenance time of the speed. This is because the risk of an accident due to negligence of the driver is greater in high-speed driving than in low-speed driving. In addition, the risk of an accident due to negligence of the driver is greater when the vehicle changes from low-speed driving to high-speed driving than when the vehicle changes from high-speed driving to low-speed driving.

Considering this, when the driving mode of the vehicle is changed, sensitivity of a decision logic about negligence of the driver may be changed (S410). This is to determine whether to provide a notification according to the number of times determined to be negligence of the driver per preset unit time.

When there is no change in the driving mode of the vehicle, sensitivity of the decision logic about negligence of the driver is maintained, and when the driving mode of the vehicle is changed, sensitivity of the decision logic about negligence of the driver may be changed (S420).

Then, occurrence of negligence of the driver and sensitivity of the decision logic about negligence of the driver are considered (S430) and whether to provide a notification to the driver may be determined (S440). The notification may be provided to the driver based on the determination (S450).

In other words, in the case of low-speed driving, changing from high-speed driving to low-speed driving, or driving of the vehicle at the same speed, sensitivity of the above-described decision logic may be somewhat lowered. For example, when three times or more are determined to be negligence of the driver within 5 seconds, the notification may be provided to the driver.

On the contrary, that is, in the case of high-speed driving or changing from low-speed driving to high-speed driving, the decision logic needs to be changed to be somewhat sensitive. For example, when twice or even once within 5 seconds is determined to be negligence of the driver, the notification may be immediately provided to the driver. Therethrough, providing an unnecessary notification to the driver may be prevented.

FIG. 9 is a diagram illustrating various embodiments of providing a notification to a driver in a driver assistance method of the present disclosure.

The present disclosure may provide the notification to the driver in various ways (S510). In particular, the notification may be provided to the driver through various stimuli.

The notification may be provided through a visual stimulus (S520), including output of a screen through a display (S521) or control of an internal lighting device (S522).

The notification may be provided through an olfactory stimulus (S530), including control of an indoor temperature by controlling the air conditioner or introduction of outside air (S531).

The notification may be provided through a tactile stimulus (S540), including control of the seat 541 (S541). The notification may be provided through an auditory stimulus (S550). This may include output of sound through the speaker (S551).

Therethrough, the driver assistance system and method using EEG according to the present disclosure may determine negligence of the driver based on the EEG signal measured by the EEG measurer and the behavior signal of the vehicle and provide the notification.

In order to increase reliability in determining negligence of the driver through the EEG signal, noise included in the EEG signal may be removed and a feature point of the EEG signal from which the noise has been removed may be extracted to determine negligence of the driver.

In addition, an unnecessary notification may be prevented from being provided by considering the behavior signal of the vehicle including driving information together with the EEG signal.

As described above, the present disclosure is directed to a driver assistance system and method. More specifically, the present disclosure provides a driver assistance system and method of determining negligence of a driver based on an electroencephalography (EEG) signal of the driver measured by an EEG measurer and a behavior signal of a vehicle and providing a notification.

As described above, the present disclosure provides a driver assistance system and method of determining negligence of a driver by removing noise included in an EEG signal and extracting a feature point of the EEG signal from which noise has been removed in order to raise reliability in determining negligence of the driver based on the EEG signal.

As described above, the present disclosure provides a driver assistance system and method of preventing an unnecessary notification from being provided by considering a behavior signal of a vehicle including driving information together with an EEG signal.

As described above, the driver assistance system and assistance method using an EEG according to the present disclosure may determine negligence of a driver based on an EEG signal of the driver measured by an EEG measurer and a behavior signal of a vehicle and provide a notification.

In addition, as described above, in order to increase reliability in determining negligence of a driver through an EEG signal, negligence of the driver may be determined by removing noise included in the EEG signal and extracting a feature point of the EEG signal from which the noise has been removed.

In addition, as described above, an unnecessary notification may be prevented from being provided by considering a behavior signal of a vehicle including driving information together with an EEG signal.

The computing apparatuses, the electronic devices, the processors, the units, the memories, and other components described herein with respect to FIGS. 1 and 6 are implemented by or representative of hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in the figures that perform the operations described in this application are performed by computing hardware, for example, by one or more processors or computers, implemented as described above implementing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions herein, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EE-PROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-Res, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. A driver assistance system using an electroencephalogram (EEG), comprising:
an EEG device comprising at least one electrode and an analog-to-digital (ADC) converter, the EEG device configured to measure an EEG signal of a driver of a vehicle; and
a processor configured to:
receive a behavior signal of the vehicle, the behavior signal including a driving mode signal indicating whether the vehicle is in a stop mode, a low-speed driving mode, or a high-speed driving mode;
filter the EEG signal to remove noise;
extract a feature point from the filtered EEG signal by analyzing a frequency component of the EEG signal;
compare the extracted feature point with one or more stored EEG signals determined to be normal to determine whether the EEG signal is a normal signal or an abnormal signal;
determine a sensitivity of a decision logic configured to provide a notification in response to a change in the driving mode signal;

determine whether to provide the notification to alert the driver based on the sensitivity of the decision logic; and
provide the notification to alert the driver in response to a determination that the EEG signal is the abnormal signal and based on the behavior signal of the vehicle.

2. The driver assistance system of claim 1, wherein the processor is further configured to determine whether the EEG signal is the normal signal based on a window size of a preset unit time.

3. The driver assistance system of claim 2, wherein the processor is further configured to control the EEG device based on the window size, in response to determining that the EEG signal is the abnormal signal.

4. The driver assistance system of claim 1, wherein the processor is further configured to:
determine whether the EEG device is normally worn or abnormally worn by the driver based on the EEG signal; and
provide another notification to the driver upon determining that the EEG device is abnormally worn by the driver.

5. The driver assistance system of claim 1, wherein the processor is further configured to provide the notification to the driver by controlling the vehicle, and wherein the notification includes one or more of an audio notification, a haptic notification, or a visual notification.

6. A processor-implemented driver assistance method for a vehicle, the method comprising:
measuring an electroencephalogram (EEG) signal of a driver of the vehicle by an EEG device comprising an electrode, an analog-to-digital (ADC) converter, and a processor;
receiving, by the processor, a driving mode signal of the vehicle that indicates one of a stop mode, a low-speed driving mode, or a high-speed driving mode;
filtering the EEG signal to remove noise;
extracting, by the processor, a feature point from the filtered EEG signal by analyzing a frequency components of the EEG signal;
determining, by the processor, whether the EEG signal is a normal signal or an abnormal signal by comparing the extracted features point to one or more stored EEG signals determined to be normal;
determining, by the processor, a sensitivity of a decision logic configured to provide a notification in response to a change in the driving mode signal;
determining, by the processor, whether to provide the notification to alert the driver based on the sensitivity of the decision logic; and
providing, by the processor, the notification to alert the driver in response to a driver negligence condition being satisfied.

7. The driver assistance method of claim 6, wherein the determination of whether the EEG signal is the normal signal or the abnormal signal is based on a window size of a preset unit time.

8. The driver assistance method of claim 7, further comprising:
controlling the EEG device based on the window size, in response to the determination of the EEG signal being the abnormal signal.

9. The driver assistance method of claim 6, further comprising:

determining whether the EEG device is normally worn by the driver based on the EEG signal; and providing another notification to the driver upon determining that the EEG device is abnormally worn.

10. The driver assistance method of claim 6, wherein the driving mode signal comprises one of a stop mode signal, a low-speed driving mode signal, or a high-speed driving mode signal, and wherein the providing of the notification comprises providing the notification in response to a number of times the driver is determined to be negligent per unit time according to the driving mode signal.

11. A method of controlling rendering, within a compartment of a vehicle, of a notification to alert a driver, the method comprising:

monitoring an electroencephalogram (EEG) signal of the driver of the vehicle and determining when the driver is in a first state and when the driver is in a second state;

receiving an indication of a driving mode of the vehicle, wherein the driving mode changes between a first mode and a second mode;

filtering the EEG signal to remove noise;

extracting a feature point from the filtered EEG signal by analyzing a frequency component of the EEG signal;

determining whether the EEG signal corresponds to the first state corresponding to a normal state or the second state corresponding to an abnormal state, by comparing the extracted features point to one or more stored EEG signals determined to be normal;

based on the driver being determined to be in the first state and the driving mode being in the first mode, performing a first rendering, within the compartment of the vehicle, of a notification to alert the driver comprising one or more of an audio notification, a haptic notification, or a visual notification; and based on the driver being determined to be in the second state and the driving mode being in the second mode, performing a second rendering, within the compartment of the vehicle, of a notification to alert the driver comprising one or more of an audio notification, a haptic notification, or a visual notification.

* * * * *